United States Patent [19]

Dean

[11] Patent Number: 4,808,156
[45] Date of Patent: Feb. 28, 1989

[54] CANNULAR INSTRUMENT AND METHOD FOR INSERTING A CANNULAR INSTRUMENT INTO A VEIN

[76] Inventor: Consuelo M. Dean, 926 S. Hillside, Wichita, Kans. 67211

[21] Appl. No.: 23,812

[22] Filed: Mar. 9, 1987

[51] Int. Cl.$^4$ ............................................. A61M 3/00
[52] U.S. Cl. .................................... 604/43; 604/164
[58] Field of Search .................. 604/44, 43, 164, 28, 604/51–53, 165, 166

[56] References Cited

U.S. PATENT DOCUMENTS

| | | | |
|---|---|---|---|
| 883,583 | 3/1908 | Stallsmisth | 604/43 |
| 4,099,528 | 7/1978 | Sorenson et al. | 604/44 |
| 4,405,313 | 9/1983 | Sisley et al. | 604/43 |
| 4,531,937 | 7/1985 | Yates | 604/164 |
| 4,540,402 | 9/1985 | Aigner | 604/44 |
| 4,568,329 | 2/1986 | Mahurkar | 604/43 |
| 4,585,435 | 4/1986 | Vaillancourt | 604/44 |
| 4,619,643 | 10/1986 | Bai | 604/43 |
| 4,682,978 | 7/1987 | Martin | 604/43 |

*Primary Examiner*—John D. Yasko
*Attorney, Agent, or Firm*—John Wade Carpenter

[57] ABSTRACT

A cannular instrument having a pair of cannulas and a pair of needles that are slidably disposed through the cannulas such that the ends of the needle extend beyond the associated ends of the cannulas. A method for inserting a cannula instrument a blood stream of an artery which includes adjusting and rotating the needles such that a facial plane on each of the beveled ends of the needles generally face in the same direction. The beveled ends of each needle and the accompanying associated ends of the two cannulas are situated within the artery and the needles may be withdrawn in order to connect to the cannulas intravenous bags holding medicinal fluids.

20 Claims, 2 Drawing Sheets

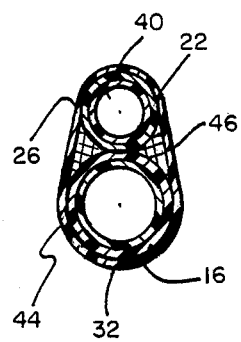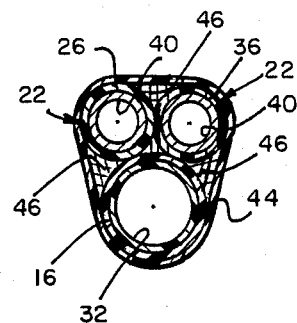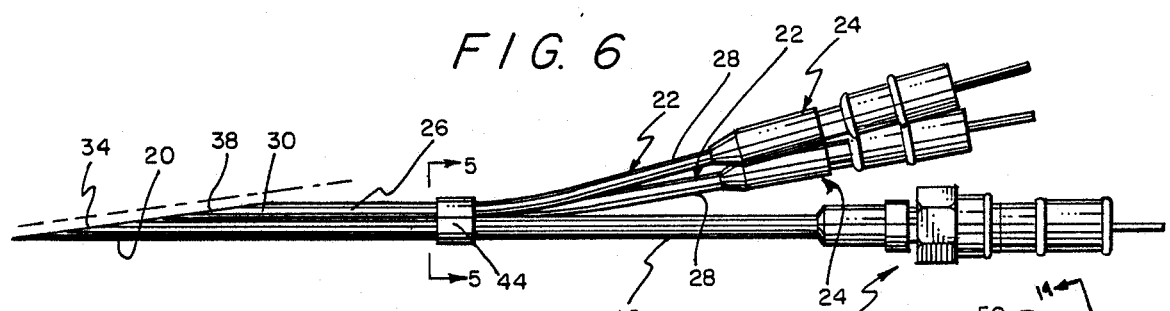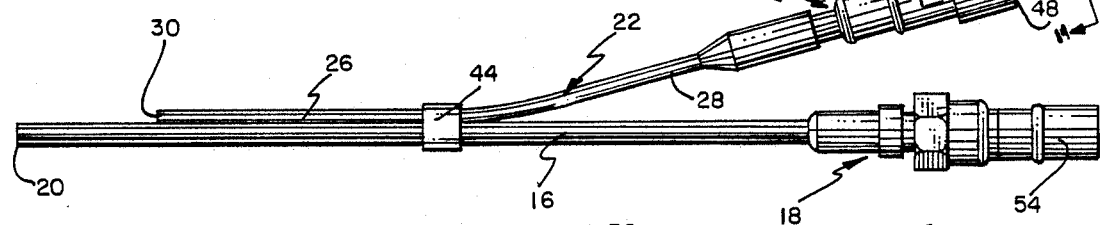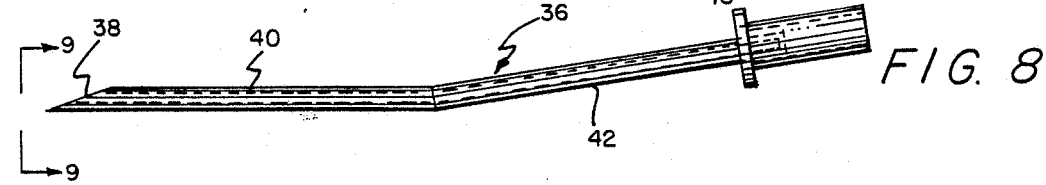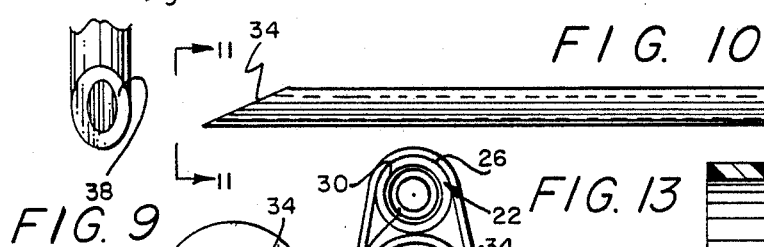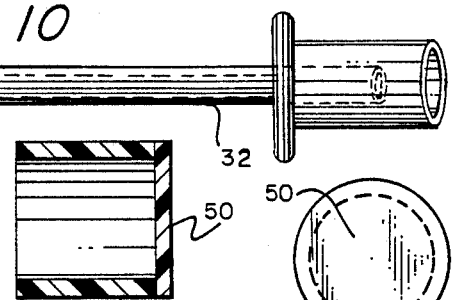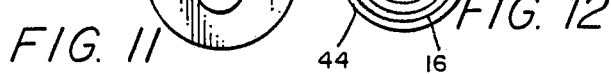

CANNULAR INSTRUMENT AND METHOD FOR INSERTING A CANNULAR INSTRUMENT INTO A VEIN

BACKGROUND OF THE INVENTION

1. Field of the Invention

This invention is related to a cannular instrument. More specifically, this invention provides a cannular instrument and a method for inserting a cannular instrument into a blood stream of a vein in order to medicinally feed the blood stream.

2. Description of the Prior Art

U.S. Pat. No. 3,804,097 to Rudie teaches a method of irrigating and treating an abcess. U.S. Pat. No. 3,841,307 by Friedell discloses a subepidermal cannular instrument and method for automated determination of bleeding time and blood loss. A dual flow cannular set is taught by Consalvo in U.S. Pat. No. 4,098,275. U.S. Pat. No. 4,134,402 by Mahurkar teaches a double lumen continuous flow hemodialysis needle and cannula. A dual lumen cannula is also illustrated and taught by Martin in U.S. Pat. No. 4,451,252. U.S. Pat. No. 4,540,402 to Aigner presents a double profusion catheter. Finally, a double lumen catheter is taught in U.S. Pat. Nos. 4,543,087 and 4,583,968 by Sommercorn et al. and Mahurkar, respectively. None of the foregoing prior art teach or suggest the particular cannular instrument and the method for inserting a cannular instrument into a blood stream of a vein, all of this invention.

SUMMARY OF THE INVENTION

The present invention accomplishes its desired objects by broadly providing a method for inserting a cannular instrument into a blood stream of a vein. The method includes passing slidably a straight rigid hollow first needle having a first needle beveled end through a unitary straight flexible first cannular means having a periphery. The first cannular means terminates into an associated first end having a facial plane that is essentially normal with respect to a horizontal plane along any point of the periphery of the entire length of the first cannular means such that the associated first end is substantially not beveled. The method also includes passing slidably respectively at least one rigid hollow second needle, having a skewed needle structure and a second needle beveled end, through at least one flexible second cannular means having a periphery and a skewed cannular structure defined by a unitary straight second cannular first part bound to the flexible first cannular means substantially along the entire length of the second cannular first part. The second cannular first part terminates into an associated second end having a facial plane that is essentially normal with respect to a horizontal plane along any point on the periphery of the entire length of the second cannular first part, and distant rearwardly from the associated first end of the first cannular means. The skewed structure of the second needle within the second cannular means is rotated and adjusted until the second needle beveled end extends beyond the associated second end and until the second needle beveled end extends from the periphery of the second cannular first part, opposite the point on the periphery of the second cannular first part where the second cannular first part connects to the first cannular means. The second needle should also be rotated and adjusted until the second needle beveled end is forward of the associated second end and slants downwardly to and terminates at a first imaginary straight line that extends longitudinally along the periphery of the first cannular means from the point on the periphery of the first cannular means where the second cannular first part connects to the first cannular means. The first needle within the first cannular means is also rotated and adjusted until the first needle beveled end extends beyond the associaed first end, and until the first needle beveled end extends from the first imaginary straight line that extends longitudinally along the periphery of the first cannular means from the point on the periphery of the first cannular means where the second cannular first part connects to the first cannular means. The first needle beveled end is further rotated and adjusted until it is forward of the associated first end and slants downwardly to and terminates at a second imaginary straight line that extends longitudinally along the periphery of the first cannular means diametrically opposite to the first imaginary straight line. The first needle beveled end and the associated first end of the first cannular means is forced on inserted into a blood stream of a vein which is to be fed medicinally. The cannular instrument is further pushed such that the second needle beveled end and the associated second end of the second cannular first part follows into the blood stream of the vein. The first needle is then withdrawn out of the vein and out of the first cannular means and the latter is attached to a first medicinal feed means in order to feed medicinally the vein through the first cannular means. The skewed structure of the second needle is likewise withdrawn out of the vein and the second cannular means and is similarly attached to a second medicinal feed means in order to feed medicinally the blood through the second cannular means. Intermittent intravenous medicinal feeding may be accomplished by disconnecting the first or the second medicinal feed means from the first or second cannular means, and then plugging the respective disconnected cannular means.

The present invention also accomplishes its desired objects by broadly providing a cannular instrument comprising in combination a unitary straight flexible first cannular means with a first cannular axis and having a periphery of which in transverse cross section generally defines a single closed plane circle at any point along the entire straight first cannular means. The unitary straight flexible cannular means terminates into an associated first end having a facial plane that is essentially normal with respect to a horizontal plane along any point on the periphery of the entire length of the first cannular means such that the associated first end is substantially not beveled. The cannular instrument further comprises at least one flexible second cannular means having a skewed cannular structure defined by a unitary straight second cannular first part with a first part axis and having a periphery which in transverse cross section generally defines a single closed plane circle. The second cannular first part is bound to the flexible first cannular means substantially along the entire length of the second cannular first part such that the first part axis is generally parallel with respect to the first cannular axis. The skewed cannular structure of the second cannular means is further defined by a second cannular second part with a second part axis and integrally bound to the second cannular first part to communicate therewith and such that the first part axis is angularly disposed with respect to the second part axis. The unitary straight second cannular first part terminates into an associated second end having a facial plane that is essentially normal with respect to a horizontal plane along any point on the periphery of the entire length of the second cannular first part. The associated second end terminates rearward of the associated first end such that the associated first end extends beyond the associated second end to prevent immediate mixing together of any medicinal fluids respectively flowing through the first cannular means and the second cannular means before the medicinal fluids enter a blood stream in an artery or vein wherein the first cannular means (more particularly the associated second end) lodge to conduct the medicinal fluids into the blood stream. The cannular instrument further includes a straight rigid hollow first needle having a first needle beveled end and which is slidably disposed through the first cannular means such that the first needle beveled end extends beyond the associated first end. At least one rigid hollow second needle having a skewed needle structure is slidably disposed through the second cannular means. The skewed needle structure of the second needle is defined by a straight rigid hollow second needle first part having a second needle beveled end and with a needle first part axis. The second needle first part is longer than the second cannular first part. The skewed needle structure is further defined by a rigid hollow second needle second part with a needle second part axis and integrally bound to the second needle first part to communicate therewith and such that the needle first part axis is angularly disposed with respect to the needle second part axis. The slidable disposition of the rigid hollow second needle within and through the second cannular means is such that the needle first part axis is generally common with the first part axis of the second cannular first part, and vice versa. Likewise, such a slidable disposition of the second needle through the second cannular means is such that the needle second part axis is common with the second part axis of the second cannular second part, and vice versa, and the second needle beveled end extends beyond the associated end. In one preferred embodiment of the cannular instrument, the facial plane of the first needle beveled end is common with the facial plane of the second needle beveled end, and vice versa.

Therefore, it is an object of the present invention to provide a cannular instrument.

It is another object of this invention to provide a method for inserting a cannular instrument into a blood stream of a vein.

It is yet another object of this invention to provide a method for medicinally feeding the blood stream of a vein.

These, together with the various ancillary objects and features which will become apparent to those skilled in the art as the following description procedes, are attained by this cannular instrument and method for inserting the cannular instrument into the blood stream of a vein, a preferred embodiment being shown with reference to the accompanying drawings, by way of example only, wherein:

BRIEF DESCRIPTION OF THE DRAWINGS

FIG. 4 is a vertical sectional view taken in direction of the arrows and along the plane of line 4—4 in FIG. 2;

FIG. 5 is a vertical sectional view taken in direction of the arrows and along the plane of line 5—5 in FIG. 6;

FIG. 6 is a is a side elevational view of another embodiment of the cannular instrument having two cannulas supported by a larger cannula including needles inserted in the respective cannulars;

FIG. 7 is a side elevational view of two cannulas without the respective needles, with the larger cannula having an intravenous tube secured to an end thereof with the shorter or smaller cannula having a cap for plugging purposes secured to an end thereof;

FIG. 8 is a side elevational view of the skewed structure of a needle that is inserted into one of the skewed cannular structures;

FIG. 9 is a front elevatonal view of the beveled end of the needle of FIG. 8 taken in direction of the arrows and along the plane of line 9—9 in FIG. 8;

FIG. 10 is a side elevational view of a unitary straight needle that is to be inserted into a straight flexible cannula;

FIG. 11 is a front elevational view of the beveled end of the straight needle of FIG. 10, taken in direction of the arrows and along the plane of line 11—11 in FIG. 10;

FIG. 12 is a front elevational view of the cannular instrument of FIG. 2 taken in direction of the arrows and along the plane of line 12—12 in FIG. 2;

FIG. 13 is a vertical sectional view of the cap that plugs one of the cannulas, taken in direction of the arrow and along the plane of line 13—13 in FIG. 7; and FIG. 14 is a top plan view of the cap of FIG. 13 taken in direction of the arrow and along the plane of line 14—14 in FIG. 7.

DETAILED DESCRIPTION OF THE INVENTION

Figure 1:
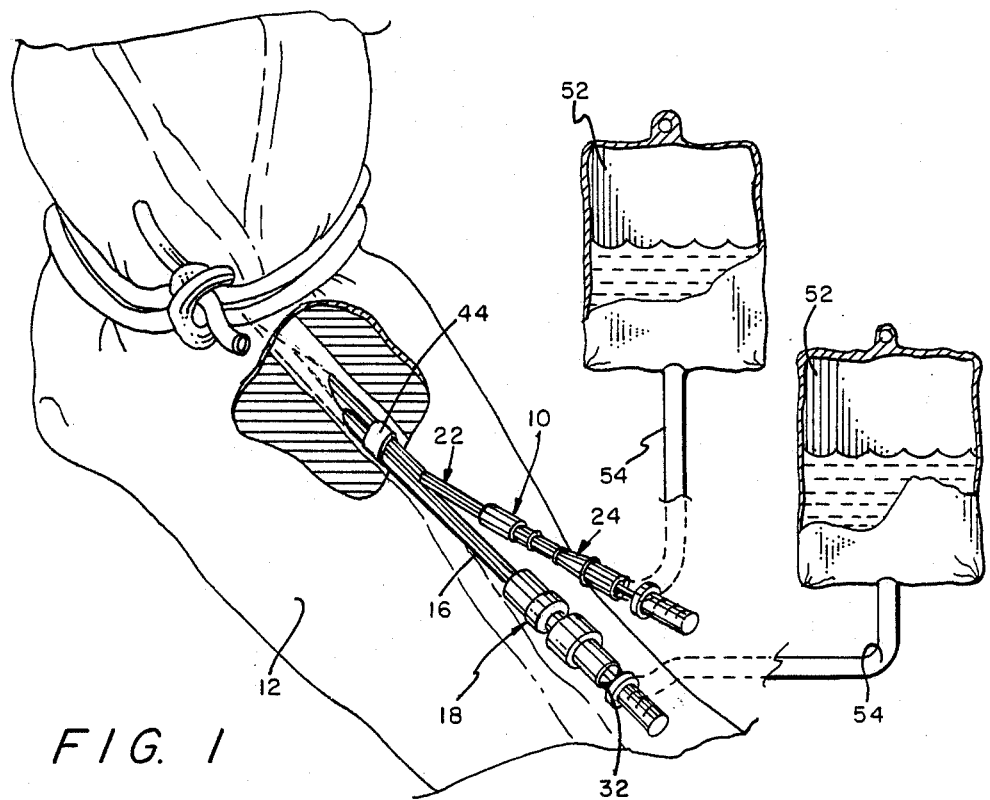
FIG. 1 is a partial perspective view disclosing the cannular instrument inserted into an arm of a patient with intravenous feeding bags with intravenous tubes disposed in proximity to the cannular instrument such that if any of the needles are withdrawn, any of the intravenous tubes may be secured to a respective cannular.

Referring in detail now to the drawings wherein similar parts of the invention are represented by like reference numerals, there is seen a cannular instrument, generally illustrated as 10, that is to be inserted through an arm 12 (or any other parts of the human body) such that the ends of the cannular instrument 10, as further clarified below, are disposed within a vein, fistula, artery 14, or the like. The cannular instrument 10 comprises a unitary, straight, flexible first cannula 16 having a head (or connecting fitting), generally illustrated as 18, and a cannula axis. The first cannula 16 has a periphery of which in transverse cross section generally defines a single closed plane circle (see FIGS. 4 and 5) at any point along the entire straight first cannula 16. The first cannula 16 terminates into an associated first end 20 that has a facial plane that is essentially normal with respect to a horizontal plane along any point on the periphery of the entire length of the first cannula 16 such that the associated first end 20 is substantially not beveled. It is believed that with such a structural configuration, as medicinal fluids exit the first cannula 16 through the non-beveled associated first end 20, turbulent flow (as opposed to laminar) occurs within the artery 14 immediately outside the non-beveled associated first end 20 (see FIG. 3).

Figure 2:
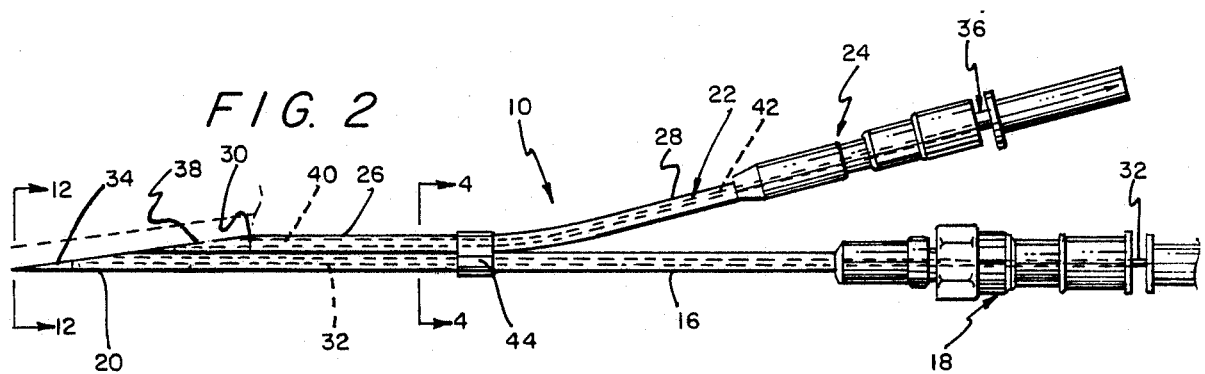
FIG. 2 is a side elevational view disclosing the cannular instrument in the preferred disposition to be inserted into a blood stream of a vein of a person, including the respective facial planes of the respective needle beveled ends being common.
Figure 3:
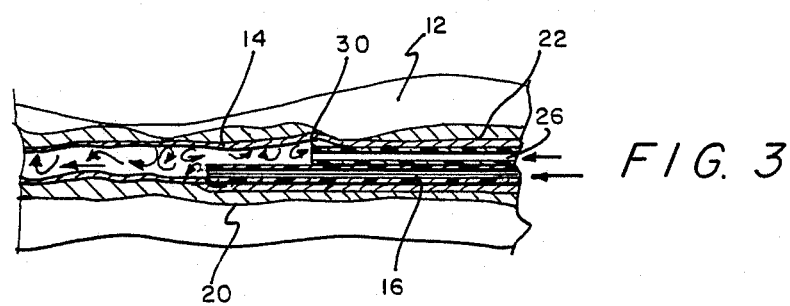
FIG. 3 is a partial side elevational view of the associated end of the two cannulas being disposed in a vein such that turbulent flow is occuring immediately outside of the respective associated ends of the two cannulas.

The cannular instrument 10 additionally comprises at least one flexible second cannula 22 (see FIGS. 5 and 6 wherein two second cannulas 22—22 are disclosed). The second cannula 22 has a head (or connecting fitting), generally illustrated as 24, and a skewed (or distorted) cannula structure that may be defined by a unitary straight cannula first part 26 with a first part axis. The first part 26 is bound to the flexible first cannula 16 substantially along the entire length of the cannula first part 26 such that the first part axis is generally parallel with respect to the first cannula axis, as illustrated in FIGS. 2, 3, and 8. The skewed cannula structure of the second cannula 22 may be further defined by a cannula second part 28 with a second part axis and integrally bound to the cannula first part 26 to communicate therewith and such that the first part axis is angularly disposed with respect to the second part axis. The cannula first part 26 terminates into an associated second end 30 that has a facial plane that is essentially normal with respect to a horizontal plane along any point on the periphery of the entire length of the cannula first part 26 such that the associated second end 30 is not beveled. As was seen for the associated first end 20, it is believed that with the associated second end 30 not being beveled, as medicinal fluids exit the second cannula 22 through the non-beveled associated second end 30, turbulent flow occurs within the artery 14 immediately outside the non-beveled associated second end 30 (as illustrated by the curvaceous arrows in FIG. 3). With the associated first and second ends 20 and 30, respectively, being constructed and disposed as such, any medicinal fluids are, ideally, quickly mixed with the blood with little or no channeling of the medicinal fluids within the blood occuring.

The associated second end 30 is also situated distantly and disposed rearwardly of the associated first end 20 such that the associated first end 20 extends beyond the associated second end 30 to prevent the immediate mixing together of any medicinal fluids respectively flowing through the first cannular 16 and the second cannula 22 before entering the blood stream within the artery 14 wherein the associated ends 20 and 30 lodge to conduct the medicinal fluids into the blood stream. This is important in these instances where medicinal fluid flowing through cannula 16 can not be premixed with medicinal fluid flowing through cannula 22, but can only be injected or emitted singularly into the blood stream.

The first cannula 16 and the at least one second cannula 22 are preferably manufactured of any flexible material including, but not limited to, Teflon ®, vinyl, polyurethane, and the like, and modifications or derivatives of these synthetics, such as vialon, etc.

The cannular instrument 10 additionally comprises a straight rigid hollow first needle 32 that has a first needle beveled end 34. The first needle 32 is slidably disposed within and through the first cannula 16 such that the first needle beveled end 34 extends beyond the associated first end 20 of the cannular 16. At least one rigid hollow second needle 36 is slidably disposed through the second cannula 22. The second needle 36 has a second needle beveled end 38 and has a skewed needle structure defined by a straight rigid hollow needle first part 40 with a needle first part axis. The needle first part 40 is longer than the cannular first part 26 such that the second needle beveled end 38 extends beyond the associated second end 30 of the cannular first part 26. The skewed needle structure is further defined by a rigid hollow needle second part 42 having a needle second part axis (see FIG. 8). The needle second part 42 is integrally bound to the needle first part 40 to communicate therewith and such that the needle first part axis is angularly disposed with respect to the needle second part axis. The rigid hollow second needle 36 is slidably disposed through the second cannula 22 such that the needle first part axis is generally common with the first part axis of the cannula first part 26, and the needle second part axis is common with the second part axis of the cannula second part 28. When the second needle 36 is disposed as such, the second needle beveled end 38 extends beyond the associated second end 30 of the second cannular 22 and there is a glove-like fit between the cannula first part 26 and the needle first part 40, and the cannular second part 28 and the needle second part 42, respectively.

The first cannula 16 and the second cannula 22 are connected and secured together by a binding agent 46 and a band 44. The binding agent 46 interconnects the entire longitudinal length of the cannula first part 26 to the first cannula 16. The binding agent should be strong enough to hold together the cannular first part 26 and the first cannular 16, as well as being compatible with the blood stream that may come in contact with the binding agent. The binding agent may be any suitable bonding glue materials or derivatives used to adhere cannulas 16 and 22, and is preferably a polyester resin system or an epoxy resin and hardener system. These are some of the glue bases known to be non-venous or non-blood damaging during use.

The band 44 surrounds the first cannula 16 and the second cannula 22 (as indicated in FIGS. 4 and 5) in order to hold the cannulas 16 and 22 together in an affixed position. As illustrated in the drawings, the band 44 is disposed around the cannula first part 26 and the first cannula 16 at the juncture of the cannula second part 28 with the cannula first part 26. By disposing the band 44 as such, the binding agent is reinforced by the outside contracting force of the band. In a preferred embodiment of the invention, the first cannula 16 has a diameter that is larger than any of the cannulas 22 which enable the band 44 to tightly encircle the cannulas 16 and 22 together, as illustrated in FIGS. 4 and 5.

With continuing reference to the drawings for the method of inserting the cannular instrument 10 into a blood stream of the artery 14 in order to feed medicinally the blood stream, the first needle 32 is slidably passed through the first cannula 16 such that the first needle beveled end 34 extends beyond the associated first end 20 of the first cannula 16. Similarly, the second needle 36 is likewise slidably passed through the second cannula 22 until the second needle beveled end 38 extends beyond the associated second end 30 of the cannula first part 26. The skewed needle structure of the second needle 36 can pass through the juncture of the cannula first part 26 and the cannula second part 28 because of the flexibility and stretching of the material (e.g. teflon, etc.) the second cannula 22 is constructed form.

After the first and second needles 32 and 36 respectively, are disposed in the respective cannulas 16 and 22, each of the needles 32 and 36 are rotated and adjusted in the following manner. The second needle 36 is adjusted such that not only the second needle beveled end 38 extends beyond the associated end 30 of the cannular first part 26, but also the second needle beveled end has its beveling structure extending from the periphery of the cannula first part 26 opposite the point of the periphery of the cannula first part 26 where the cannula first part 26 connects to the first cannula 16, forward of the associated second end 30 and sloping downwardly to and terminating at a first imaginary straight line that extends longitudinally along the periphery of the first cannula 16 from the point on the periphery of the first cannula 16 where the cannula first part 26 connects or is bound to the first cannula 16.

Similarly, the first needle 32 is rotated and adjusted such that not only the first needle beveled end 34 extends beyond the associated first end 20 of the first cannula 16, but also the beveling structure of the first needle beveled end 34 extends from the first imaginary straight line that extends longitudinally along the periphery of the first cannula 16 from the point on the periphery of the first cannula 16 where the cannula first part 26 connects to the first cannula 16, forward of the associated first end 20 and sloping downwardly and terminating at a second imaginary straight line that extends longitudinally along the periphery of the first cannula 16 diametrically opposite the first imaginary straight line. In a more preferred embodiment of the invention, when the respective needles 32 and 36 are situated as such, each of the respective needle beveled ends 34 and 38 has a facial plane that would be common with the facial plane of each other. Stated alternatively, when the needles 32 and 36 are rotated and adjusted as previously mentioned, the first needle beveled end 34 has a facial plane that would be common with a facial plane of the second needle beveled end 38, and the second needle beveled end 38 would have a facial plane that would be common with the facial plane of the first needle beveled end 34, as illustrated by the dotted line across the needle beveled ends 34 and 38 in FIGS. 2 and 6.

When the respective needles 32 and 36 have been rotated and adjusted as such, the first needle beveled end 34 is forced and inserted into the artery 14 of a person. Such force and insertion causes the associated first end 20 of the first cannula 16 to also be inserted and forced into the artery 14. The cannular instrument 10 is continually pushed and forced such that the second needle beveled end 38, and its concomitant associated second end 38 of the second cannula 22, follow into the same artery 14. After the cannular instrument 10 has been disposed as such, blood may be withdrawn from the artery 14 through either needle 32 or needle 36. It is not necesary to the method of this invention that blood be withdrawn through either of the two needles 32 or 36, but such may be preferred to insure that the needle beveled ends 34 and 38, and their accompanying cannula associated ends 20 and 30, respectively, are indeed in the artery 14.

In one embodiment of the method of this invention, the second needle 36 is withdrawn out of the artery 14 and the second cannula 22 and is plugged with a cap 48 to prevent the flow of blood from the artery 14, through the second cannula 22 and out of the second cannula 22 and into the environment. It should be noted, that cap 48 may also be used to plug not only the second cannula 22 but also the first cannular 16.

The cap 22 is disposed around the head or the connecting fitting 24 of the second cannula 22 (or the first cannula 16). The cap 48 has a piercable membrane-like head 50 that is exposed at the end of the second cannula 22 (or the first cannula 16). At any point of time, this piercable membrane-like head 50 may be pierced with a needle or stillette in order to form an opening to introduce medicinal fluids therethrough such that the second cannula 22 (or the first cannula 16) may conduct the same into the artery 14. Medicinal fluids are generally maintained in intravenous bags 52 (see FIG. 1) that include an intravenous tube 54 which may be connected to heads 18 or 24 of the first cannula 16 or the second cannula 22, respectively, in order for medicinal fluids to flow therethrough.

Alternatively, the second needle 36 may be merely withdrawn out of the second cannula 22 (without plugging the head 24 with a cap 48) and immediately or shortly thereafter the head 24 is secured to one of the intravenous tube 54 in order to feed medicinally the blood into the artery 14 through the second cannula 22.

The method of inserting the cannular instrument 10 into the artery 14 additionally comprises withdrawing the first needle 32 out of the artery 14 and the first cannula 16, and attaching the intravenous tube 54 to the head 18 of the first cannula 16 in order to feed medicinally therethrough the blood. The intravenous tubes 54—54 (see FIG. 1) may be connected to the respective cannula heads 18 and 24 at any point in time, and disconnected from such to plug or cap the respective cannulas 16 or 22 in order than only one of the cannulas 16 or 22 may be employed to feed medicinally the blood. As was previously indicated, any plugged or capped cannulas 16 or 22 may be unplugged or uncapped by merely piercing the piercable membrane-like head 50 in order to medicinally feed the fluids through a respective cannulas 16 or 22. Thus, the method of this invention is ideally suited for the intermittent intravenous feeding of medicinal fluids.

While the present invention has been described herein with reference to particular embodiments thereof, a latitude of modification, various changes and substitutions are intended in the foregoing disclosure, and it will be appreciated that in some instances some features of the invention will be employed without a corresponding use of other features without departing from the scope of the invention as set forth.

I claim:

1. A method for inserting a cannular instrument into a blood stream of a vein comprising the steps of
    (a) forming a straight rigid hollow first needle having a first needle beveled end;
    (b) forming at least one rigid hollow second needle having a skewed needle structure and a second needle beveled end;
    (c) passing slidably the straight rigid hollow first needle through a unitary straight flexible first cannula having a periphery and terminating in an associated first end having a facial plane that is essentially normal with respect to a horizontal plane along any point on the periphery of the entire length of the first cannula such that the associated first end is substantially not beveled;
    (d) passing slidably respectively said at least one rigid hollow second needle through at least one flexible second cannula having a periphery and a skewed cannular structure defined by a unitary straight second cannular first part bound to said flexible first cannula substantially along the entire length of the second cannular first part and terminating in an associated second end having a facial plane that is essentially normal with respect to a horizontal plane along any point on the periphery of the entire length of the second cannular first part and distant rearwardly from the associated first end of the first cannula;

(e) rotating and adjusting the skewed structure of the second needle within the second cannula until the second needle beveled end extends beyond the associated second end and the second needle beveled end further extends from the periphery of the second cannular first part opposite the point on the periphery of the second cannular first part where the second cannular first part connects to the first cannula, forward of the associated second end and down to and terminating at a first imaginary straight line that extends longitudinally along the periphery of the first cannula from the point on the periphery of the first cannula where the second cannular first part connects to the first cannula;

(f) rotating and adjusting the first needle within the first cannula until the first needle beveled end extends beyond the associated first end and the first needle beveled end extends from the first imaginary straight line that extends longitudinally along the periphery of the first cannula from the point on the periphery of the first cannula where the second cannular first part connects to the first cannula, forward of the associated first end and down to and terminating at a second imaginary straight line that extends longitudinally along the periphery of the first cannula diametrically opposite to the first imaginary straight line;

(g) forcing the first needle beveled end and the associated first end of the first cannula into a blood stream of a vein which is to be fed medicinally; and (h) forcing subsequently the second needle beveled end and the associated second end of the second cannula first part into the blood stream of the vein of step (g).

2. The method of claim 1 additionally comprising withdrawing blood from the blood stream of the vein through the first needle after step (h).

3. The method of claim 2 additionally comprising withdrawing blood from the blood stream of the vein through the skewed structure of the second needle after step (h).

4. The method of claim 3 additionally comprising terminating the withdrawing of blood through the second needle; withdrawing the second needle out of the vein and the second cannula; and plugging the second cannula with a cap to prevent the flow of blood from the vein, through the second cannula and out of the second cannula means into the environment.

5. The method of claim 4 additionally comprising withdrawing the first needle out of the vein and the first cannula; and attaching a first medicinal feed to the first cannula means in order to feed medicinally the blood.

6. The method of claim 5 additionally comprising piercing the cap of the second cannula; and attaching the pierced cap to a second medicinal feed means in order to feed medicinally the blood through the pierced cap and through the second cannula.

7. The method of claim 1 additionally comprising withdrawing the second needle out of the vein and the second cannula.

8. The method of claim 7 additionally comprising attaching a first medicinal feed to the second cannula in order to feed medicinally the blood through the second cannula.

9. The method of claim 1 additionally comprising withdrawing the first needle out of the vein and the first cannula; and attaching a first medicinal feed means to the first cannula in order to feed medicinally the blood through the first cannula.

10. The method of claim 1 additionally comprising plugging the second cannula with a cap.

11. The method of claim 10 additionally comprising withdrawing the first needle out of the vein and the first cannula; and attaching a first medicinal feed to the first cannula means in order to feed medicinally the blood through the first cannula.

12. The method of claim 1 additionally comprising withdrawing the first needle out of the vein and the first cannula; and attaching a first medicinal feed means to the first cannula in order to feed medicinally the blood through the first cannula; and withdrawing the skewed structure of the second needle out of the vein and the second cannula; and attaching a second medicinal feed means to the second cannula in order to feed medicinally the blood through the second cannula.

13. The method of claim 12 additionally comprising disconnecting the second medicinal feed means from the second cannula and then plugging the second cannula.

14. A cannular instrument comprising in combination a unitary straight flexible first cannula with a first cannula axis and having a periphery of which in transverse cross section generally defines a single closed plane circle at any point along the entire straight first cannula, said unitary straight flexible cannula terminates in an associated first end having a facial plane that is essentially normal with respect to a horizontal plane along any point on the periphery of the entire length of said first cannula such that the associated first end is substantially not beveled;

at least one flexible second cannula having a skewed cannular structure defined by a unitary straight second cannular first part with a first part axis and having a periphery of which in transverse cross section generally defines a single closed plane circle and bound to said flexible first cannula substantially along the entire length of the second cannular first part such that said first part axis is generally parallel with respect to said first cannula axis and further defined by a second cannular second part with a second part axis and integrally bound to said second cannular first part to communicate therewith and such that said first part axis is angularly disposed with respect to said second part axis, said unitary straight second cannular first part terminates in an associated second end having a facial plane that is essentially normal with respect to a horizontal plane along any point on the periphery of the entire length of the second cannular first part and further terminating rearward of said associated first end such that said associated first end extends beyond the associated second end to prevent the immediate mixing together of any medicinal fluids respectively flowing through the first cannula and the second cannula before entering a blood stream in a vein wherein the first cannula and the second cannula lodges to conduct the medicinal fluids into the blood stream;

a straight rigid hollow first needle having a first needle beveled end and slidably disposed through said first cannula such that said first needle beveled end extends beyond said associated first end;

at least one rigid hollow second needle having a skewed needle structure defined by a straight rigid hollow second needle first part with a needle first part axis and longer than said second cannular first part and having a second needle beveled end and further defined by a rigid hollow second needle second part with a needle second part axis, said rigid hollow second needle is slidably disposed through said second cannula such that said needle first part axis is generally common with said first part axis of said second cannular first part and said needle second part axis is common with said second part axis of said second cannular second part and said second needle beveled end extends beyond said associated second end.

15. The cannular instrument of claim 14 additionally comprising a band means surrounding said first cannula and said at least one second cannula to hold the same together in an affixed position.

16. The cannular instrument of claim 15 wherein said first cannula and said second cannular first part are bound together with a bonding agent.

17. The cannular instrument of claim 16 wherein said first cannula additionally comprises a first hollow cannular head secured to an end opposed to the associated first end and wherethrough said first needle slidably passes.

18. The cannular instrument of claim 17 wherein said second cannula additionally comprises a second hollow cannular head secured to said second cannular second part and wherethrough said second needle with its skewed structure slidably passes.

19. The cannular instrument of claim 18 wherein said closed plane circle of said second cannular first part has a smaller diameter then the diameter of the closed plane circle of the first cannula.

20. The cannular instrument of claim 19 wherein said first needle beveled end comprises a first needle facial plane that is common with a second needle facial plane of the second needle beveled end.

* * * * *